(12) United States Patent
Adam

(10) Patent No.: US 7,771,359 B2
(45) Date of Patent: Aug. 10, 2010

(54) ENHANCEMENT OF ULTRASONIC CAVITATION

(75) Inventor: Dan Adam, Haifa (IL)

(73) Assignee: Venousonics Ltd., Zemach (IL)

( * ) Notice: Subject to any disclaimer, the term of this patent is extended or adjusted under 35 U.S.C. 154(b) by 109 days.

(21) Appl. No.: 11/568,970

(22) PCT Filed: May 5, 2005

(86) PCT No.: PCT/IL2005/000478

§ 371 (c)(1),
(2), (4) Date: Jul. 9, 2007

(87) PCT Pub. No.: WO2005/107600

PCT Pub. Date: Nov. 17, 2005

(65) Prior Publication Data

US 2008/0045835 A1  Feb. 21, 2008

Related U.S. Application Data

(60) Provisional application No. 60/569,255, filed on May 10, 2004.

(51) Int. Cl.
A61B 8/14 (2006.01)
(52) U.S. Cl. ........................ 600/458; 600/437
(58) Field of Classification Search ............ 601/2; 600/458, 439
See application file for complete search history.

(56) References Cited

U.S. PATENT DOCUMENTS

| | | | |
|---|---|---|---|
| 5,219,401 A * | 6/1993 | Cathignol et al. | 600/439 |
| 5,694,936 A | 12/1997 | Fujimoto et al. | |
| 5,827,204 A * | 10/1998 | Grandia et al. | 601/2 |
| 5,935,142 A | 8/1999 | Hood | |
| 6,413,216 B1 | 7/2002 | Cain | |
| 6,508,774 B1 * | 1/2003 | Acker et al. | 601/2 |
| 7,347,855 B2 | 3/2008 | Eshel et al. | |

(Continued)

FOREIGN PATENT DOCUMENTS

EP 0701840 A1 3/1996

(Continued)

OTHER PUBLICATIONS

Shin-ichiro Umemura et al., "Enhancement of Sonodynamic Tissue Damage Production by Second-Harmonic Superimposition: Theoretical Analysis of Its Mechanism," IEEE Transactions on Ultrasonis, Ferroelectrics, and Frequency Control, vol. 43, No. 6, Nov. 1996, pp. 1054-1062.

(Continued)

*Primary Examiner*—Long V Le
*Assistant Examiner*—Joel F Brutus
(74) *Attorney, Agent, or Firm*—Lowe Hauptman Ham & Berner, LLP

(57) ABSTRACT

A two step method of enhancing the cavitational effect produced by ultrasonic signals focused at a specific location in a medium includes a first step of using one or more transducers to apply the ultrasonic signals to create a waveform that causes formation of bubbles at the location, and a second step of modulating the amplitude of the ultrasonic signals at a frequency of several Hz to several tens of kilohertz immediately following or coincident with the formation of the bubbles.

15 Claims, 13 Drawing Sheets

U.S. PATENT DOCUMENTS

2002/0009015 A1*  1/2002  Laugharn et al. ............ 366/108
2003/0018256 A1   1/2003  Sasaki et al.

FOREIGN PATENT DOCUMENTS

WO     2005/074365 A2    8/2005

OTHER PUBLICATIONS

Ruo Feng et al., "Enhancement of ultrasonic cavitation yield by multi-frequency sonication," Ultrasonics Sonochemistry 9 (2002), pp. 231-236.

Shin-ichiro Umemura et al., "In vitro and in vivo enhancement of sonodynamically active cavitation by second-harmonic superimpostion," J. Acoust. Soc. Am. 101 (1), Jan. 1997, pp. 569-577.

EP Search Report for EP05738990.0 mailed Nov. 18, 2009.

* cited by examiner

ENHANCEMENT OF ULTRASONIC CAVITATION

RELATED APPLICATIONS

The present application is a National Phase entry of International Application Number PCT/IL2005/000478, filed May 5, 2005, which claims priority from, U.S. Provisional Application No. 60/569,255, filed May 10, 2004, the disclosures of which are hereby incorporated by reference herein in their entirety.

FIELD OF THE INVENTION

The present invention relates to the field of ultrasound technology. Specifically the invention relates to a system for creating ultrasound waves and focusing them at a location in a medium and to methods for enhancing the resultant cavitational effects that take place in the focal region.

BACKGROUND OF THE INVENTION

The use of ultrasound for medical diagnostics and therapy is well known. Diagnostic techniques are based on the production and transmission of ultrasound waves into the body, and detection of the scattered echoes from the scanned region. Therapeutic methods are generally based on the use of focused beams of ultrasonic energy to produce high-powered mechanical energy for disintegration of medical targets by heat and ablation or cavitation caused by pressure waves. In body fluids such as blood or in the intercellular fluids in living tissue, the application of ultrasonic energy often leads to the creation of bubbles which grow in volume by a process known as rectified diffusion and eventually implode releasing large amounts of energy and generating sites of locally high temperature and pressure for very short periods of time.

In industry cavitational effects are used for a wide variety of applications from cleaning of objects to initiating chemical reactions.

Conventional ultrasound signals are generated by transducers powered by a sinusoidal waveform such as that shown in FIG. 1. The horizontal axis represents time measured in μsec and the vertical axis the voltage applied to the transducer. When the applied electrical signal is in the frequency range of the transducer's frequency bandwidth and the signal is at least a few cycles long, the pressure wave generated by the transducer is of similar shape. The waves that are emitted from the transducer travel through the media as longitudinal waves (the transverse waves usually attenuate very rapidly in tissue and thus are ignored herein) having alternating compression and de-compression regions corresponding to the positive and negative portions of the waveform shown in FIG. 1. When the wave passes through a fluid, gases trapped inside dust motes or other particles in the fluid, or on the walls of the region containing the fluid will be drawn out from the fluid forming a small bubble. If the acoustic power density is small, then the bubble will oscillate around a relatively constant radius. This process is known as stable cavitation. If the power density is high, then gas diffuses into the bubble during the de-compression half-cycle of the sound waves and diffuses out from the bubble during the compression half-cycle. The rate of diffusion is proportional to the radius of the bubble and therefore the rate of diffusion into the bubble (which occurs when the bubble has expanded during the de-compression phase) exceeds that of the rate of diffusion out of the bubble (which occurs when the bubble has been compressed). The net result is that the radius of the bubble increases as the bubble oscillates. This process is known as rectified diffusion. Once the bubble's radius reaches a critical value, which depends on the power and frequency of the ultrasonic energy, it can no longer remain stable and the pressure caused by the next compression half-cycle will cause the bubble to implode, i.e. the fluids in the vicinity of the bubble oscillate with such an amplitude that the bubble breaks into small fractions.

In medical applications the energy released by the implosion of the bubbles in the rectified diffusion process is used to destroy near by cells. Various methods are known to produce cavitation at the desired location. For example, U.S. Pat. No. 5,219,401 teaches the use of relatively low power ultrasound energy to produce stable cavitation resulting in a population of bubbles at a site and then applying a second signal at another frequency and higher power to cause the bubbles to implode. U.S. Pat. No. 6,413,216 teaches the use of an unfocused transducer operating at a low frequency to create bubbles in a treatment area of a patient followed by the use of a focused ultrasound beam at a different frequency aimed at a specific region within the treatment area in order to cause cavitation and thereby create a lesion at a desired location. U.S. Pat. No. 5,827,204 teaches a method reported to produce large vaporous cavitation bubbles in a small confined area. The method comprises generating a low frequency signal having amplitude less than the cavitation threshold to produce a population of bubbles and superimposing on this signal a high frequency signal. The amplitude of the resulting modulated signal exceeds the cavitation threshold at the focus of the modulated beam. The aim of the art is to increase the magnitude of the cavitational effect while at the same time carefully controlling the region in which cavitation takes place in order to allow more precise therapeutic treatment while preventing unintended damage to surrounding cells In recent years it has been shown that sonochemically active cavitation can be enhanced an order of magnitude by superimposing the second harmonic onto the fundamental in insonation [S. Umemara, K. Kawabata, and K. Saski: "Enhancement of Sonodynamic Tissue Damage Production by Second-Harmonic Superimposition: Theoretical Analysis of its Mechanism", IEEE Transactions on Ultrasonics, Ferroelectricss and Frequency Control, 43 (1996) 1054-1062]; and [S. Umemara, K. Kawabata, and K. Saski: "In vitro and in vivo enhancement of sonodynamically active cavitation by second-harmonic superimposition" J. Acoust. Soc. Am. 101 (1997) 569-577.] In another study it has been shown that combined irradiation with two or more orthogonal beams, of different ultrasound frequencies focused at a common location produces a significant increase in cavitation effects over single frequency irradiation. [Ruo Feng, Yiyun Zhao, Changping Zhu, T. J. Mason: "Enhancement of ultrasonic cavitation yield by multi-frequency sonification", Ultrasonics Soinochemistry 9 (2002) 231-236.]

It is a purpose of the present invention to provide an apparatus and method for providing focused ultrasonic waves having a waveform at the focal point that is modified to cause enhanced cavitation.

Further purposes and advantages of this invention will appear as the description proceeds.

SUMMARY OF THE INVENTION

The invention is a method of enhancing the cavitational effect produced by ultrasound signals focused at a specific location in a medium. The method of the invention comprises two steps:

(a) using one or more transducers to apply the ultrasound signals to create a waveform that causes formation of bubbles at the location; and (b) modulating the amplitude of the ultrasound signals at a frequency of several Hz to several tens of kilohertz immediately following or coincident with the formation of the bubbles.

According to the method of the invention, the frequency of the modulation is preferably between 5 KHz and 25 KHz. The modulation can be carried out either by combining of two or more interfering primary beams emitted from two or more transducers having a common focus or by exciting individual transducers by an excitation pulse composed of two excitation pulses with closely proximate frequencies.

In preferred embodiments of the invention, the waveform causing the production of bubbles is either a sinusoidal waveform or a waveform comprising high negative peaks and small positive peaks.

According to the preferred embodiment of the method of the invention, if the number of transducers is more than one, then the different frequencies emitted by the transducers are integral multiples of the lowest of the frequencies. In an embodiment three transducers are used to carry out the invention.

The radius of the microbubbles is typically in the range from a fraction of a micron up to 100 or more microns, preferably from approximately 3 microns to 5 microns.

In preferred embodiments of the invention, an ultrasound imaging or non-imaging system is used to view and monitor the region being targeted, to monitor the generation of the microbubbles at the desired location, and control the system for one or more of the following purposes:

(a) for aiming the focused beam to enable generating the microbubbles at the targeted location;

(b) to insure that the number of microbubbles is as planned;

(c) to re-align the beam to a different location; and (d) to monitor the formation, maintenance, or implosion of the microbubbles for the purpose of controlling either continuously or intermittently the application of the waveform and/or the modulation signals that causes these processes in order to achieve the planned result.

The response at the half harmonic or at higher harmonics of the transmitted frequencies can be used by the ultrasound imaging or non-imaging system to measure the number of microbubbles generated within the targeted region and their spatial distribution.

In preferred embodiments of the invention the multiple transducers are arranged as an array, designed so that their mechanical focus and their own focus combine at the same point in space. In one preferred embodiment, the array is an annular array. Preferably the ultrasonic waves transmitted by the different transducers are designed to produce in the microbubbles at the focal point interference that generates specific waveforms at specific frequencies and amplitudes, which are not produced at other locations and the focal point can be moved axially or laterally by either shifting the whole array, by repositioning of individual transducers, or by phase shift of the excitation pulse. In preferred embodiments of the invention, the region within the focal zone of all the transducers in which the specific waveform develops at significant intensities and the amplitudes of the waveforms are less than −3 DB of the maximum amplitude, are typically at distances less than 25 mm and preferably less than 1 mm away from the point of the maximum amplitude in the lateral directions and less than 10 mm and preferably less than 1.5 mm away in the axial directions.

The method of the invention for the localized production of bubbles at a location and the enhancement of the cavitational and implosion effects that take place at that location can be used for therapeutic purposes. For this use the one or more transducers are placed extra-corporally, in close proximity to the organ to be treated, with a spacer made of ultrasound-transparent material, ultrasound gel, or water surrounding the ultrasound transducer/s and filling the space between it and the surface of the body overlying the organ.

All the above and other characteristics and advantages of the invention will be further understood through the following illustrative and non-limitative description of preferred embodiments thereof, with reference to the appended drawings.

DETAILED DESCRIPTION OF PREFERRED EMBODIMENTS

The enhanced cavitational effects, i.e. improving microbubble generation, oscillation, changes in bubble size, and implosion, achieved by use of the present invention are the result of applying a relatively low frequency waveform to the region of interest. The theoretical and practical difficulty that must be overcome is to focus the waveform to a sufficiently small region, for example in human veins or in tissue underlying the skin, in order to obtain useful therapeutic results. The invention solves this problem by using a two-step approach. In the first step, ultrasonic energy, from one or more transducers, is focused at the region of interest and bubbles are formed. In the second step, which follows immediately after or coincident with the formation of the bubbles, ultrasonic signals are applied, which are so designed so as to produce modulated amplitude at a relatively low frequency of several Hz to several tens of kilohertz, thereby providing the desired low frequency waveform, which is confined to the non-linear region created by the bubbles formed in the first step. In the presently preferred embodiments of the invention, frequency of the modulation is between 5 kHz and 25 kHz.

The low frequency waveform can be produced either by combination of two or more interfering primary beams emitted from two or more transducers having a common focus or alternatively from individual transducers excited by an excitation pulse composed of two excitation pulses with closely proximate frequencies.

The first step of the method of the invention is carried out using one or more energy transducers, each operating at a different frequency, which is typically in the range of several hundreds of KHz. In order to take advantage of the enhanced effects noted in the prior art, at least two transducers should be used and their frequencies should be related such that they are harmonics of each other.

In the first method of producing the waveform for the second step of the invention, at least two transducers are used where one frequency is supplied to one transducer, e.g. 1.00 MHz, and a frequency different by several Hz to several tens of KHz is supplied to the second transducer, e.g. 1.01 MHz. This produces at the target location, i.e., where bubbles have been formed during the first step of the method of the invention, pressure fields at relatively low frequencies that are typically on the order of several Hz to several tens of KHz, e.g. 10 kHz.

Figure 2:
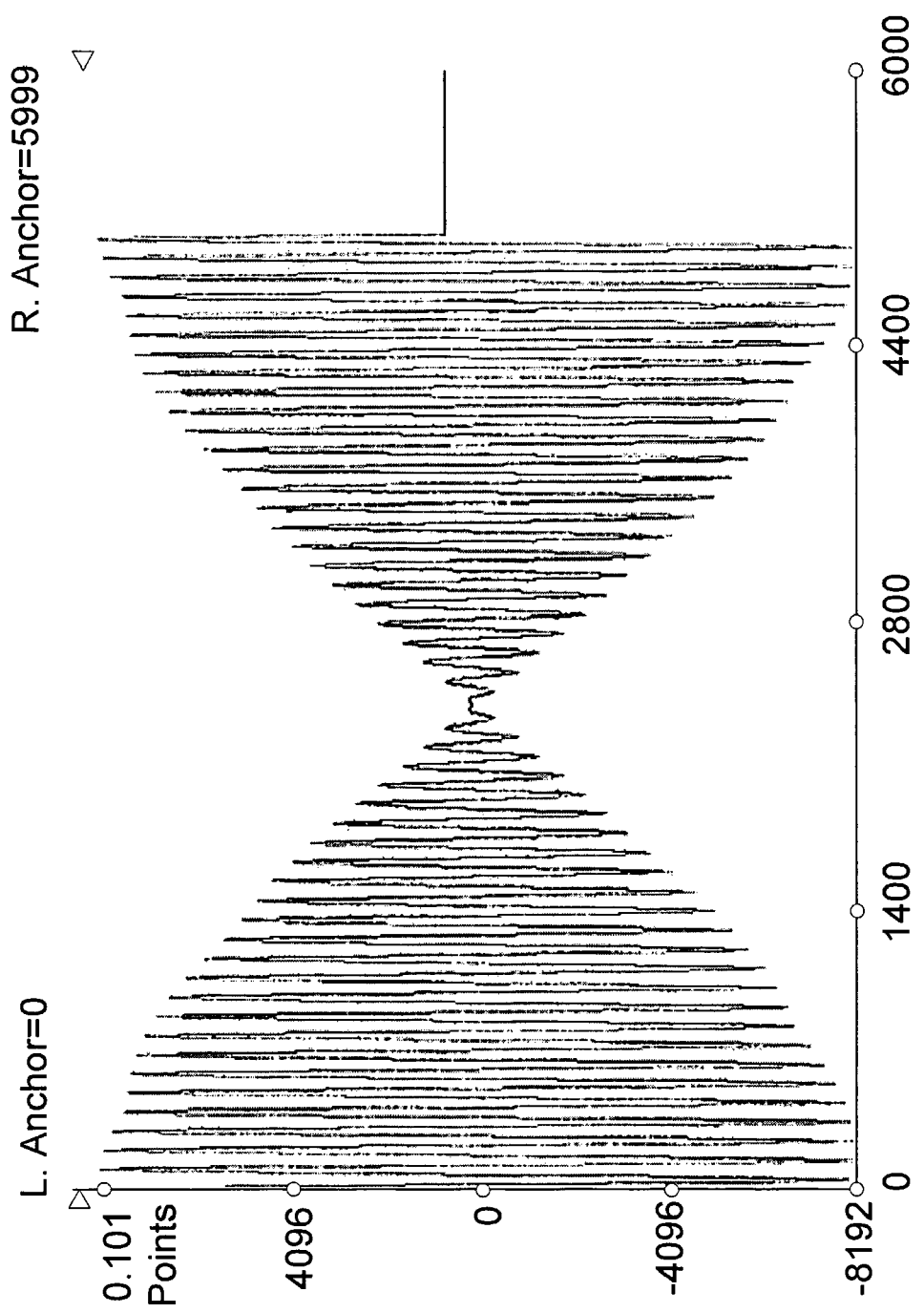
FIG. 2 shows a waveform supplied to a transducer produced by a combination of a 1.00 MHz and a 1.01 MHz signal.

In the second method of producing the waveform, the relatively low frequencies are also produced only at the location of treatment, i.e. where microbubbles have been generated during the first step. As an example of the second method, one frequency supplied to the transducer could be 1 MHz and the second frequency 1.01 MHz. This produces an ultrasonic wave having a frequency of approximately 1 MHz, with a varying phase and with an amplitude modulation of 10 kHz. This waveform is shown in FIG. 2. Due to the highly nonlinear behavior of the bubbles generated in the first step of the method of the invention, a "detection" phenomenon takes place in the focal region and in the region occupied by the bubbles, which is exposed to ultrasonic waves of 1.0 MHz and 1.01 MHZ, there is generated ultrasonic waves of ~10 KHz and ~2.01 MHz. This results in non-linear enhancement of the cavitational effect; i.e. the cavitational effect of the resultant sonication at the relatively low frequencies is larger than the algebraic sum of the effects of each component at the relatively high frequencies (e.g. 1.0 MHz, 1.01 MHz, 2.01 MHz and their harmonics).

Co-pending International Patent Application PCT/IL2005/000128 by the same inventor, the description of which, including reference cited therein, is incorporated herein by reference in its entirety, describes a system and method for using ultrasound waves that are focused at a specific location in a medium to cause localized production of bubbles at that location and to control the production, and the cavitational and heating effects that take place there. Much of the apparatus and methods described in this application can be usefully adapted to carry out the present invention.

To produce the waveforms in PCT/IL2005/000128, at least three independent high-power focused ultrasound transducers are used, housed within a structure that produces a common focus. Each transducer is powered by its own amplifier, which is driven by a signal generator, usually tuned to a different frequency. Optionally the system for producing the waveforms may also include a control system that measures the changes in tissue or the size of the bubbles and accordingly adjusts the waveform.

Figure 3:
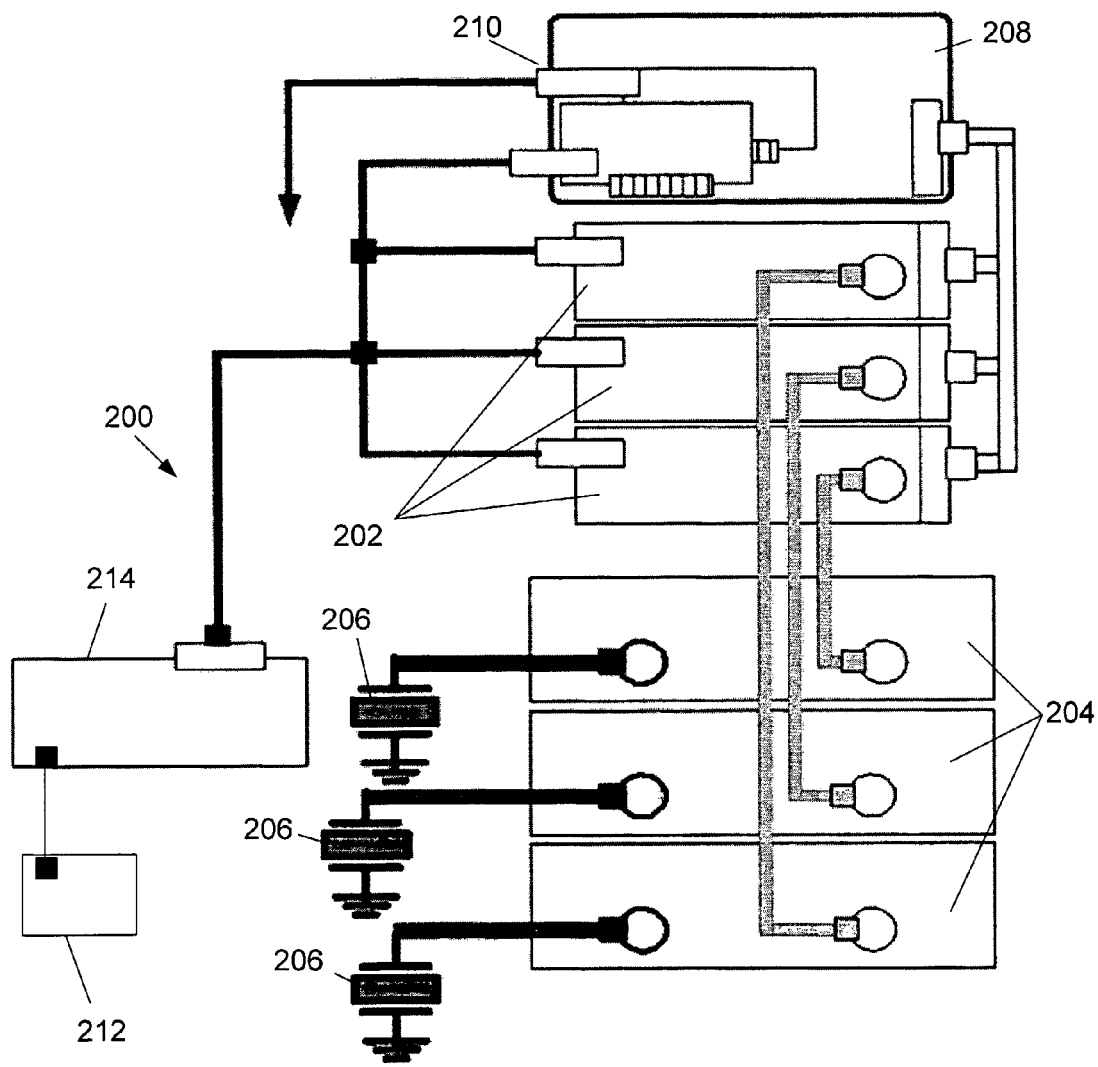
FIG. 3 schematically shows an example of a control and driving system for carrying out the invention.

One embodiment of the control and driving system that can also be used for carrying out the present invention is shown schematically in FIG. 3. In this embodiment, the control and driving system 200 includes three arbitrary waveform signal generators 202 connected to three wide-band power amplifiers 204 and, through impedance matching, to the three transducers 206. At least one workstation 208, for example a personal computer (PC), controls the timing of activation and amplitude of each arbitrary waveform signal generator 202 by means of different protocols and separate cables for each signal generator. The workstation 208 may also control a temperature measurement system 210 that measures and records temperatures, for example with thermocouples. Additionally or alternatively, an ultrasound imaging or non-imaging system 212 may be used to view and monitor the region being treated (targeted) to monitor the generation of the microbubbles at the desired location and control the system so that the number of microbubbles will be as planned and/or may be used for aiming the focused beam to the targeted region and/or to re-align the beam to a different location. The cavitation effects can be detected by many different techniques that are known to skilled persons. For example: use of a single transducer operating at $\frac{1}{2}$, $\frac{1}{3}$, $\frac{1}{4}$, etc. of the frequency of one of the transducers in the array as a detector; use of a single transducer operating at 1.5, 2.5, 3.5, etc. harmonic; use of a "white noise" detector; use of a pair of transducers working continuously as a transmitter-receiver pair; or use of a single transducer, that both transmits and receives the reflected signal. The ultrasound system monitoring system 212 may be controlled by the workstation 208 to which it is connected through control box 214.

Control and driving system 200 is comprised of standard components that are well known to persons familiar with the use of ultrasound for diagnostic or therapeutic purposes. Typical but non-limitative examples of commercially available components that are suitable for use in control and driving system 200 are: arbitrary waveform signal generator 202—Tabor Electronics Ltd., model 8025; wide-band 10 kHz-100 MHz power amplifier 204—Acoustic Research, model 150A100B; transducer 206—Imasonic, model no. T3035A101, T3034A101, T2336A101; workstation 208—HP-Compaq PC; temperature measurement system 210—Omega thermocouples, model no. TGC150-CPSS-150-SMP-MUK270502, National Instruments Temperature measurement board model no. NI-4351, Temperature I/O box model no. TC-2190, and National Labview software; ultrasound imaging system 212—GE Healthcare model VIVID III; and control box 214—HP-Compaq PC running National Instruments Labview software, National Instruments I/O box, model no. BNC-2090, and National Instruments DAQ board model no. PC-LPM-16.

The power transducers 206 are arranged as an array, designed so that their mechanical focus and their own focus combine at the same point in space. This point in space can be moved by either shifting the whole array, by repositioning of individual transducers, or by phase shift of the excitation pulse. The ultrasonic waves transmitted by the different transducers are designed to produce by interference specific waveforms at the focal point, which are not produced at other locations. The region in which the specific waveforms develop at significant intensities, i.e. within the focal zone of all transducers, is usually very small, where the amplitudes of −3 DB and less of the maximum, are typically less than 1 mm away from the point of maximum in the lateral directions and, less than 1.5 mm away in the axial directions.

Figure 4A:
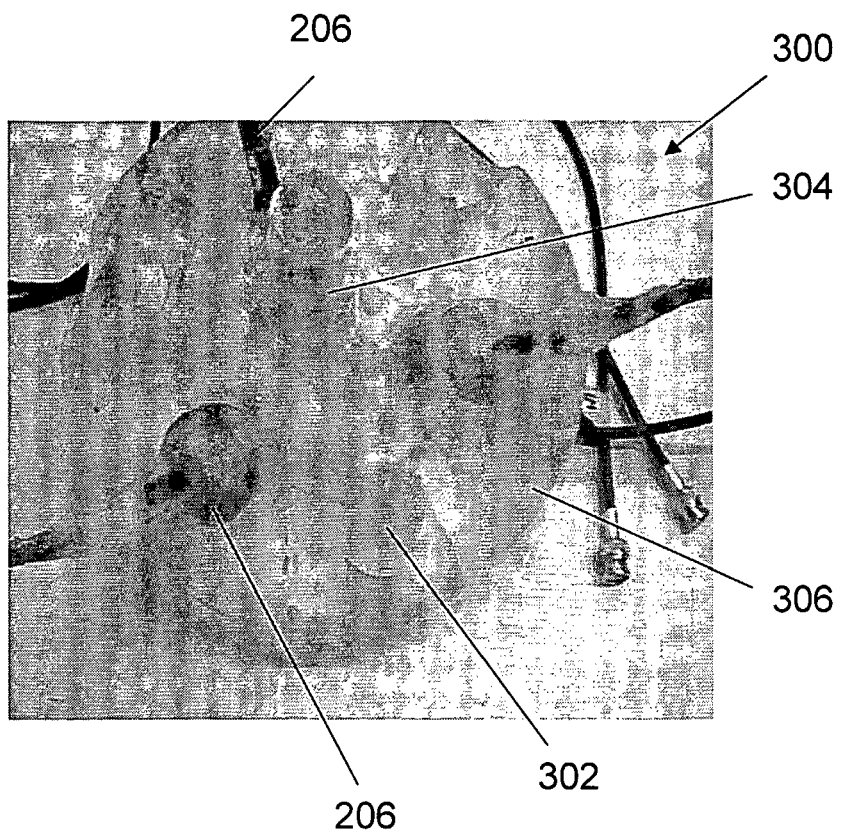
FIG. 4A and FIG. 4B show an embodiment of an array of transducers that is suitable for use in carrying out the invention.
Figure 4B:
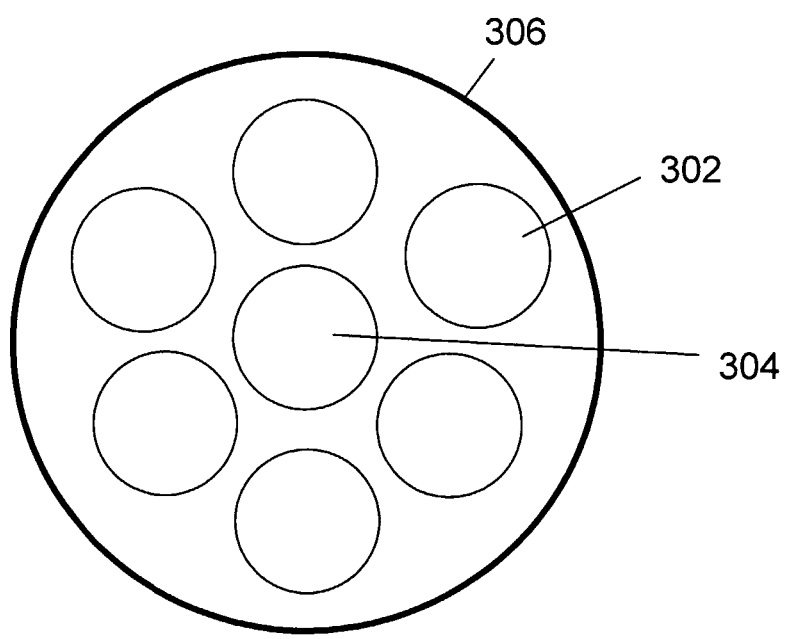

An embodiment of an array of transducers 300 that uses cylindrical power transducers suitable for use in the invention is shown in FIG. 4A and FIG. 4B. Another embodiment, using annular transducers is described with reference to FIG. 5A to 5D hereinbelow. FIG. 4A is a photograph showing the array 300 from the top. Array 300 is mounted in a cylindrically shaped holder 306 made of plexiglass or other suitable material. In the embodiment shown, holder 306 comprises a central bore 304 coaxial with the symmetry axis of holder 306 and six other bores 302 arranged symmetrically around bore 304 and inclined at an angle with the symmetry axis. Array of transducers 300 can thereby comprise up to six cylindrical power transducers 206 which are inserted into bores 302 such that all are physically aimed at the same focal point. The focal point of the array of ultrasound transducers 300 depends, upon other factors on the medium through which the ultrasound waves will be transmitted. A typical focal distance in water for array 300 is six cm from the bottom face of transducer holder 306. This focal distance is equivalent to five cm in gel and four cm in liver tissue. The center bore 304 can be used for an imaging probe connected to an imaging system 212 or for inserting thermocouples that are components of temperature measurement system 210. FIG. 3B schematically shows the arrangement of the bores 302 and 304 on the planar bottom face of holder 306.

The holder 306 is designed such that array 300 can be placed extra-corporally, in close proximity to the organ to be treated, with ultrasound-transparent material, ultrasound gel, or water surrounding the ultrasound transducers and filling the space between it and the organ.

As mentioned hereinabove, ultrasound system 200 may be either imaging or non-imaging and in the preferred embodiment of the invention is used to measure the number of microbubbles, their location in space, and their spatial population distribution. These measurements can be made during any phase of the process, for example when bubbles are generated during the cavitation phase, during a heating phase, a phase when it is desired to reduce or enlarge the size and/or number of microbubbles, or during microbubble destruction usually by implosion.

The goals of the invention are achieved by selecting the range of parameters, including frequency, phase, and amplitude, of each one of the multiple transducers to produce the desired waveform in the region of interest. Bubbles having a size ranging from a fraction of a micron up to 100 or more microns can be produced using the system described herein. The presently preferred range for the bubble size for therapeutic use is between approximately 3 to 5 microns. Similarly the size of the focal area can be varied between spots that are typically less than 25 mm radius, and preferably less than 1 mm, radius in the lateral directions and less than 10 mm, and preferably less than 1.5 mm, long in the axial directions. The ability to achieve such a small focal zone length in the axial direction by using the method and apparatus of the invention provides a significant improvement in the ability to provide localized treatment for various conditions over the prior art methods in which the focal zone length typically ranges between 10 mm and 20 mm. The minimum size of the treatment area is on the order of the minimum size of the focal area and, by means of electrically or mechanically scanning the combined beams and/or the array of transducers, the maximum size of the treatment area is unlimited.

Figure 5A:
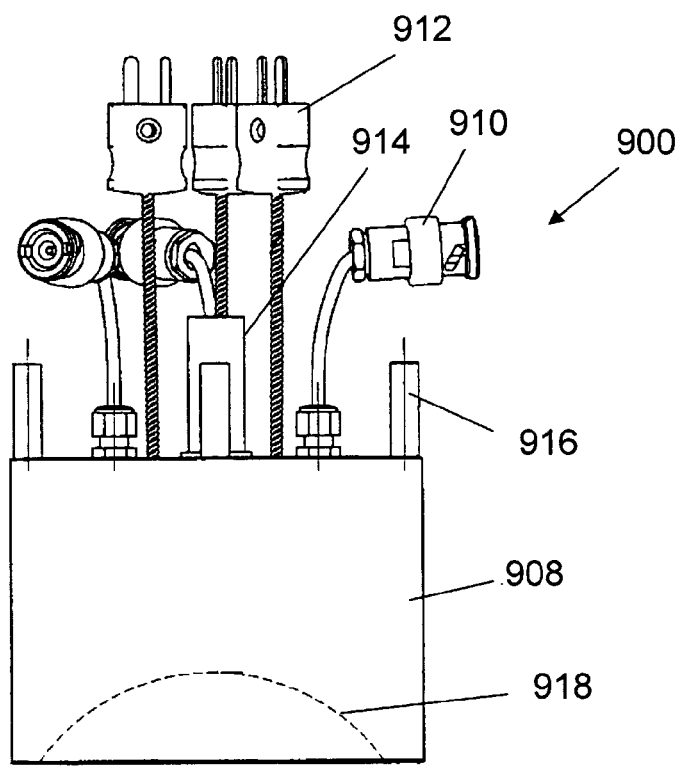
FIG. 5A to FIG. 5D show an embodiment of an annular array of transducers that is suitable for use in carrying out the invention.
Figure 5B:
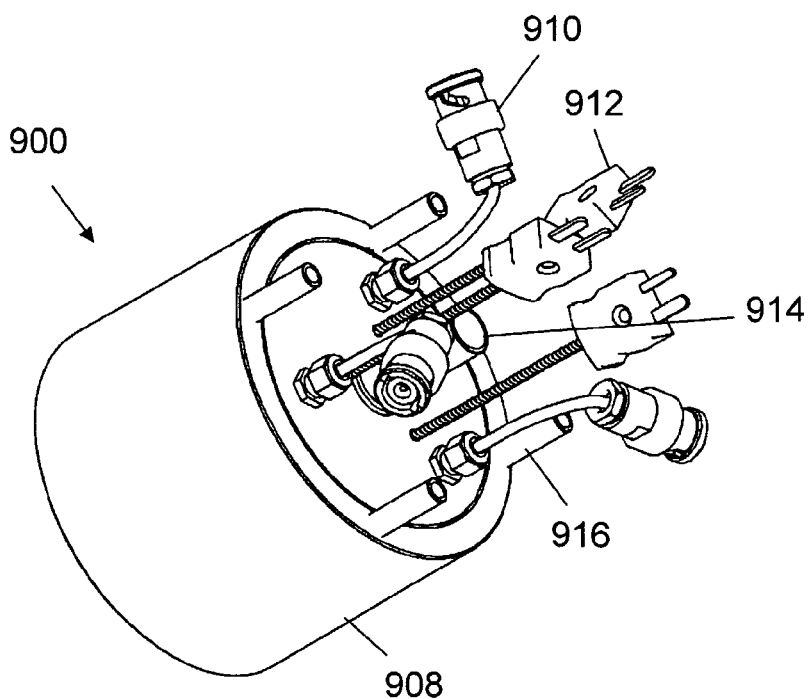
Figure 5C:
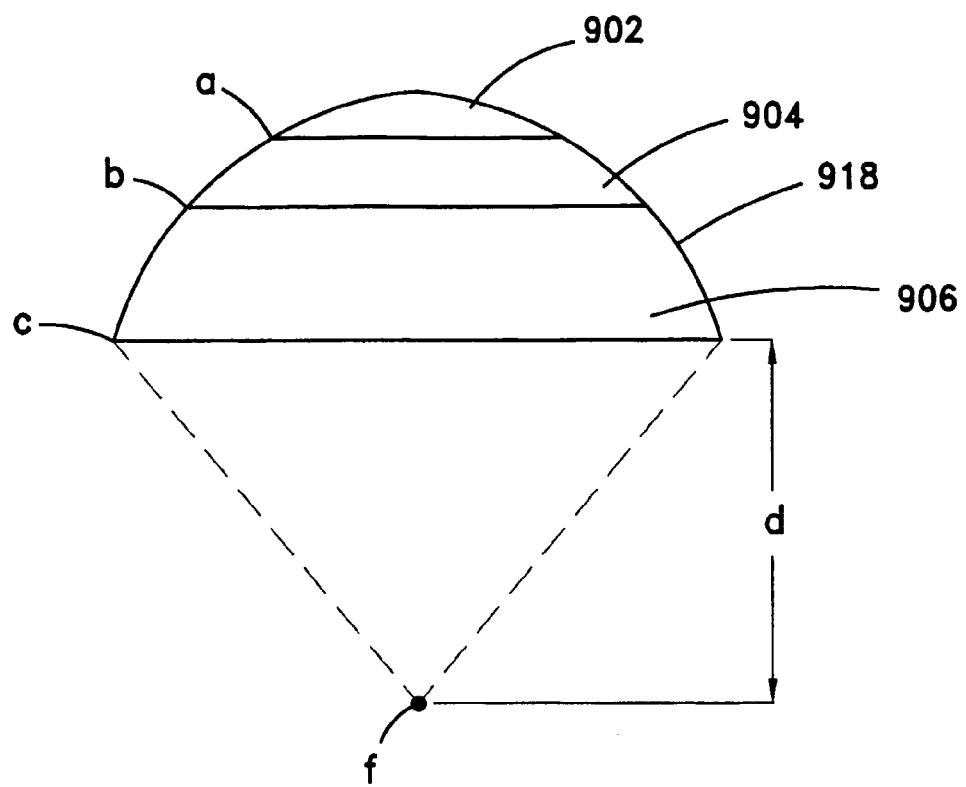
Figure 5D:
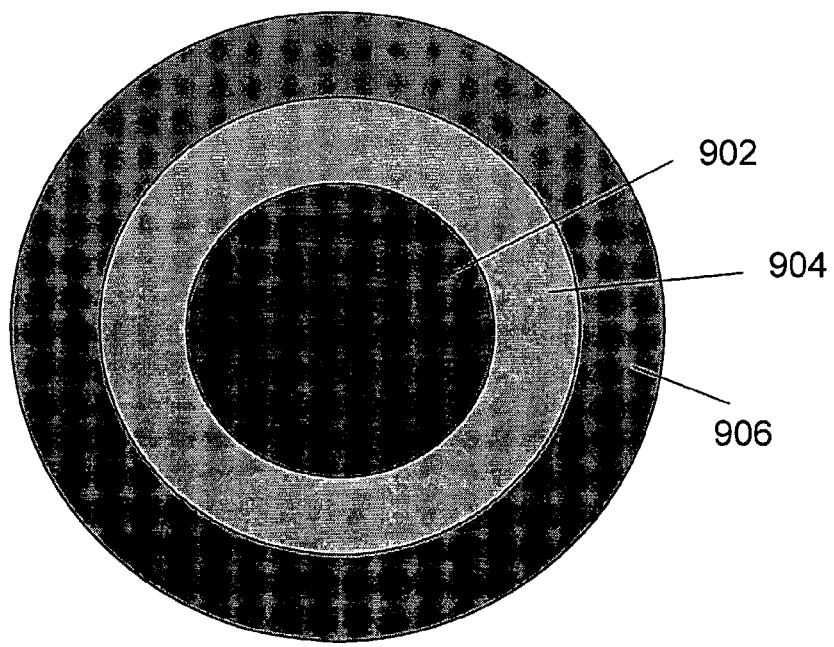
Figure 6:
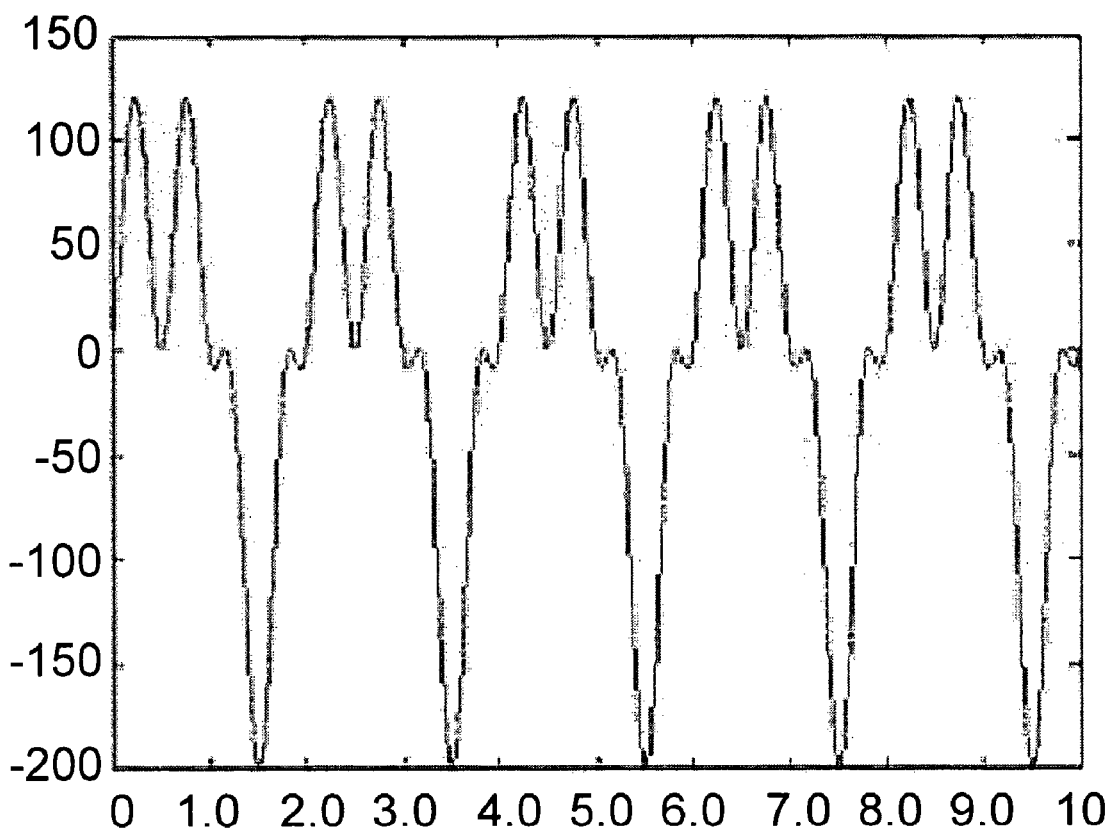
FIG. 6 shows a waveform comprising high amplitude negative peaks and small amplitude positive peaks that is useful for carrying out the first step of the method of the invention.

FIG. 6 shows a waveform comprising high negative peaks and small positive peaks. This type of waveform, by increasing the ratio of the amplitudes of the de-compression part of the acoustic wave to the compression part, encourages the creation of a cloud of microbubbles. This type of waveform is most effective for carrying out the first step in the method of the current invention. In FIG. 6, the horizontal axis represents time measured in μsec and the vertical axis the amplitude of the signal at the focus measured in volts. The signal shown in FIG. 6 was generated, using the system shown in FIG. 3 and the array shown in FIG. 4A comprising three transducers, by a hydrophone that converts accurately the acoustic pressure at that point to volts. The control and driving system operated at the frequencies, phases, and amplitudes shown in Table 1 in order to produce the waveform shown in FIG. 5.

TABLE 1

| Transmission frequency | Output Voltage of Signal Generator | Output Voltage of Power Amplifier | Gain setting of Power Amplifier | Phase of the signal |
| --- | --- | --- | --- | --- |
| 0.5 MHz | 180 mV | 165 V | 90% | 0° |
| 1.0 MHz | 100 mV | 80 V | 90% | 90° |
| 2.0 MHz | 100 mV | 37 V | 100% | 270° |

Another embodiment of a transducer array that can be used to carry out the method of the invention is shown in FIGS. 5A to 5D. FIG. 5A is a side view and FIG. 5B a perspective view showing the features of the outside of cylindrical holder 908 of array 900. Shown in these figures are three connectors 910 for the power cables to the three transducers and three connectors 912 for thermocouples. The thermocouples in array 900 are placed on the rear sides of each of the transducers to monitor their performance during the development stage of the array. They are not necessary features of a commercial array. Also shown on the top of holder 908 is air inlet 914 and air outlets 916, which are provided to pass air over the backs of the transducers and remove heat from the inside of holder 908.

As opposed to the array 300 shown in FIGS. 4A and 4B, which comprises cylindrical transducers 206, the array 900 is comprised of three annular transducers 902, 904, and 906. The three transducers are arranged such that their front faces form a spherical shaped active area 918, which focuses the energy from all of the transducers at the same point below the bottom of the holder. The common focal point (f in FIG. 5C) is located on the vertical symmetry axis of holder 908 and is the center of curvature of spherical active area 918.

FIG. 5C is a cross-sectional view showing the arrangement of the three transducers. Lines a, b, and c are respectively the bottom edges of transducers 902, 904, and 906. The bottom of transducer 902 and the inner side surfaces of transducers 904 and 906 define the spherical active surface 918. Line c also represents the bottom edge of holder 908 and therefore the "skin plane", when the array is placed on a patient's body during a therapeutic procedure. The distance from the skin plane to the focus f is designated by the letter d. FIG. 5D is a view from the bottom of the array showing the location of transducers 902, 904, and 906 on the active surface 918.

An illustrative, but nor limitative, example of the dimensions of an array 900 designed for therapeutic treatment is: height and diameter of holder 908 are 65 mm and 88 mm respectively; radius of curvature of the spherical active surface 918 is 45 mm; and distance d is 27 mm. The frequencies of the transducers in the array are 350 KHZ, 700 KHZ, and 1050 KHZ. It is to be noted that the ratio of these frequencies is 1:2:3. This is different from the ratio 1:2:4 of array 300, which was described hereinabove. This illustrates that the invention is not limited to any particular frequencies or for that matter to using three transducers; however, in order to enhance the cavitation results, it is important that if more than one transducer and/or frequency is used then the different frequencies emitted by the transducers should preferably be integral multiples of the lowest frequency. The main consideration in choosing the number, frequencies, and other parameters of the transducers and other components of the system is the waveform of the signal that is to be produced by the array in order to achieve the intended results.

The method of the invention for enhancing cavitation effects at a specific location in a medium is carried out using an ultrasonic energy generator system such as 200 in FIG. 3 in the following manner:

(a) A generator of ultrasonic waves is placed on the outer surface of the medium and directed towards the specific location. The generator can comprise dual track transducers or an array of two or more transducers such as those described hereinabove.

Figure 1:
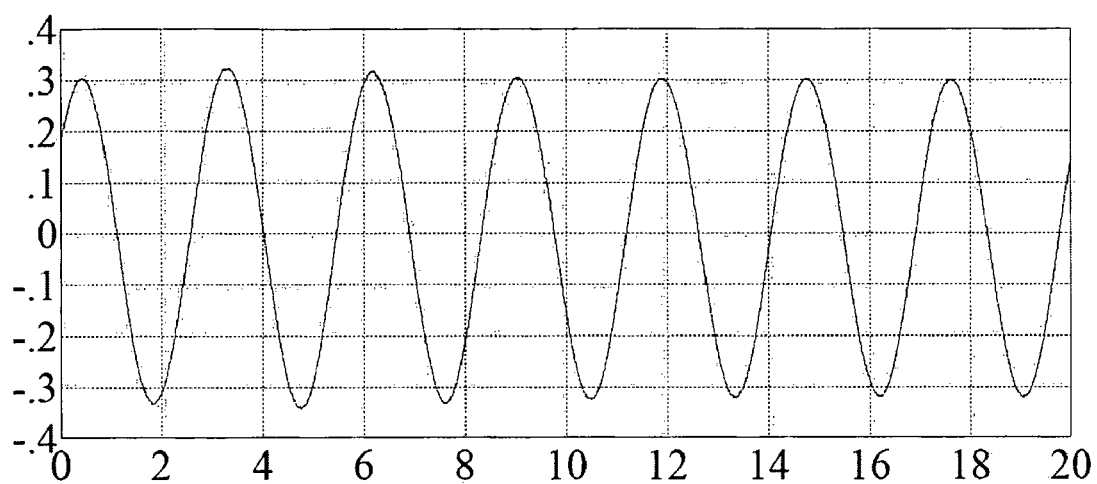
FIG. 1 shows an ultrasound signal having a sinusoidal waveform.

(b) Ultrasonic energy is applied to the transducer/s to produce a waveform that generates gas bubbles at the focal point by rectified diffusion. The process of bubble formation can be further enhanced by using two or more frequencies that are harmonics of each other. The size of the focal area can be more accurately controlled by using three or more transducers to produce the waveform shown in FIG. 6 than if the sinusoidal waveform shown in FIG. 1 is used.

(c) Immediately following, or coincident with the formation of the bubbles, the amplitude of the elements is modulated at a relatively low frequency (e.g. 5 kHz-25 kHz).

Step (c) can be carried out in one of the following two ways:

(i) by applying a waveform having two close frequencies to each pair of transducers, e.g. for an array of four transducers, the transducers could be operated at 0.5 MHz, 0.51 MHz, 1.0 MHz, and 1.01 MHz respectively;

(ii) by driving each transducer with a signal comprised of proximate frequencies, e.g. for the annular array described hereinabove, the three transducers could be operated at 350 KHZ and 360 KHz, 700 KHZ and 710 KHz, and 1050 KHZ and 1060 KHz respectively.

The method can be carried out with several variations. For example:

Steps (b) and (c) can be carried out sequentially.

Step (c) can be initiated after bubble formation however step (b) does not cease when step (c) begins and then the two steps are carried out simultaneously. This mode of performing the invention can be carried out by using a different transducer or array to provide the signals needed for each of the two steps or by using a single array in which the signals from at least some of the transducers are alternated between the different waveforms.

The signals can be applied sequentially but cyclically; i.e. step (b) (bubble formation) followed by step (c), which is carried out until a decline in activity is observed, followed by step (b), which produces a sufficient quantity of bubbles to make step (c) effective, followed by step (c), etc.

An ultrasound imaging or non-imaging system can be used to view and monitor the region being targeted, to monitor the generation of the microbubbles at the desired location, and to control the system, either manually or automatically, for one or more of the following purposes:

(a) for aiming the focused beam to enable generating the microbubbles at the targeted location;

(b) to insure that the number of microbubbles is as planned;

(c) to re-align the beam to a different location; and (d) to monitor the formation, maintenance, or implosion of the microbubbles for the purpose of controlling either continuously or intermittently the application of the waveform and/or the modulation signals that causes these processes in order to achieve the planned result.

The method of the invention is especially well suited for therapeutic purposes. For such uses, the one or more transducers are placed extra-corporally, in close proximity to the organ to be treated, with a spacer made of ultrasound-transparent material, ultrasound gel, or water surrounding the ultrasound transducer/s and filling the space between it and the surface of the body overlying the organ.

Experiments

Experiments have been carried out in order to demonstrate the two-step method of the invention. The following examples are provided merely to illustrate the invention and are not intended to limit the scope of the invention in any manner.

Experiment 1

Figure 7A:
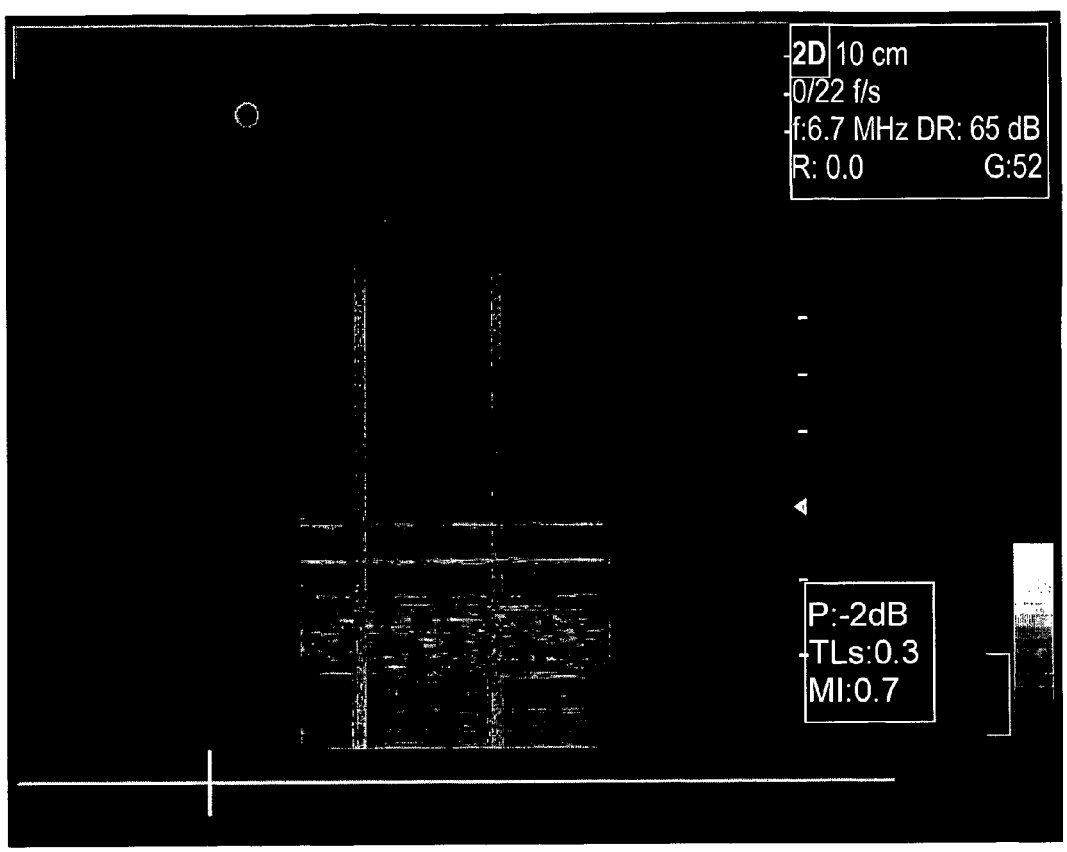
FIG. 7A and FIG. 7B are images which demonstrate the two-step method of the invention.
Figure 7B:
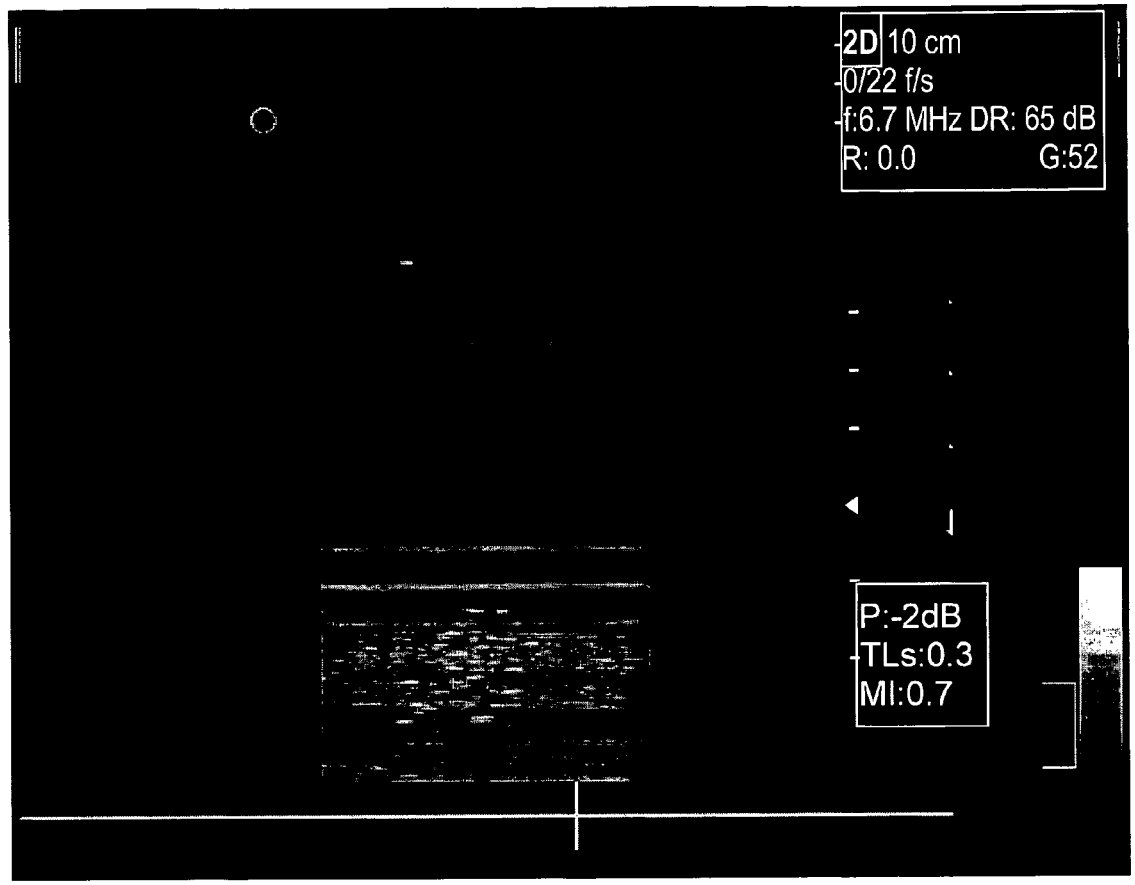

An experiment was done in water, using a special latex tube mimicking a vein. The energy produced by three transducers arranged in an annular array as shown in FIGS. 5A to 5D and operating at 350 kHz, 700 kHz, and 1050 kHz was focused in the water within the tube and bubbles were produced as shown in FIG. 7A. Following the step of bubble production, the transmission of the two higher frequency transducers was stopped and the 350 kHz transducer was driven at 350 kHz and 360 kHz. The enhanced cavitation effects produced in this step can be observed in FIG. 7B. The images in FIGS. 7A and 7B were acquired by a Vivid III imaging system with a 7L Linear array.

Experiment 2

FIGS. 8A, 8B, 9A, and 9B are power spectrum of echoes obtained by hydrophone from a sample of fat insonated by the array of transducers used in Experiment 1. In each of these figures the vertical axis represents the power and the horizontal axis the frequency. The upper curve is the "raw" data and the lower curve shows the results after filtering and normalization.

Figure 8A:
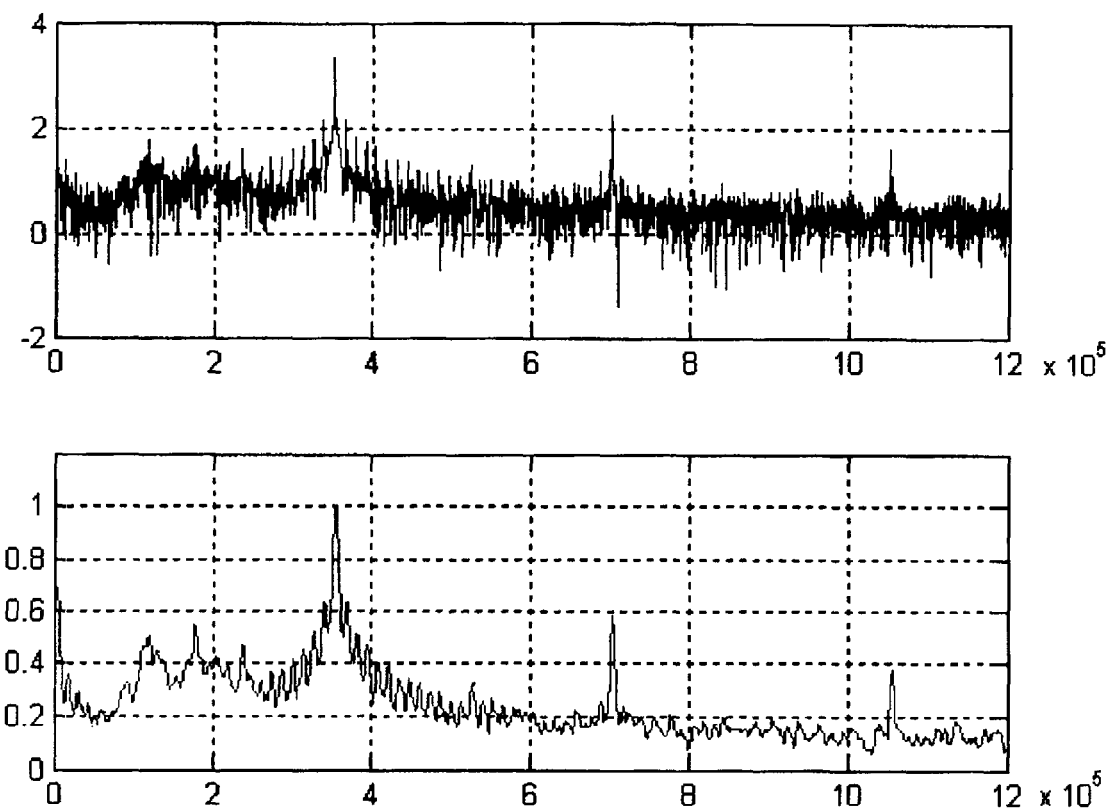
FIG. 8A and FIG. 8B are power spectrum of the echoes from microbubbles produced in fat in step one of the method of the invention.
Figure 8B:
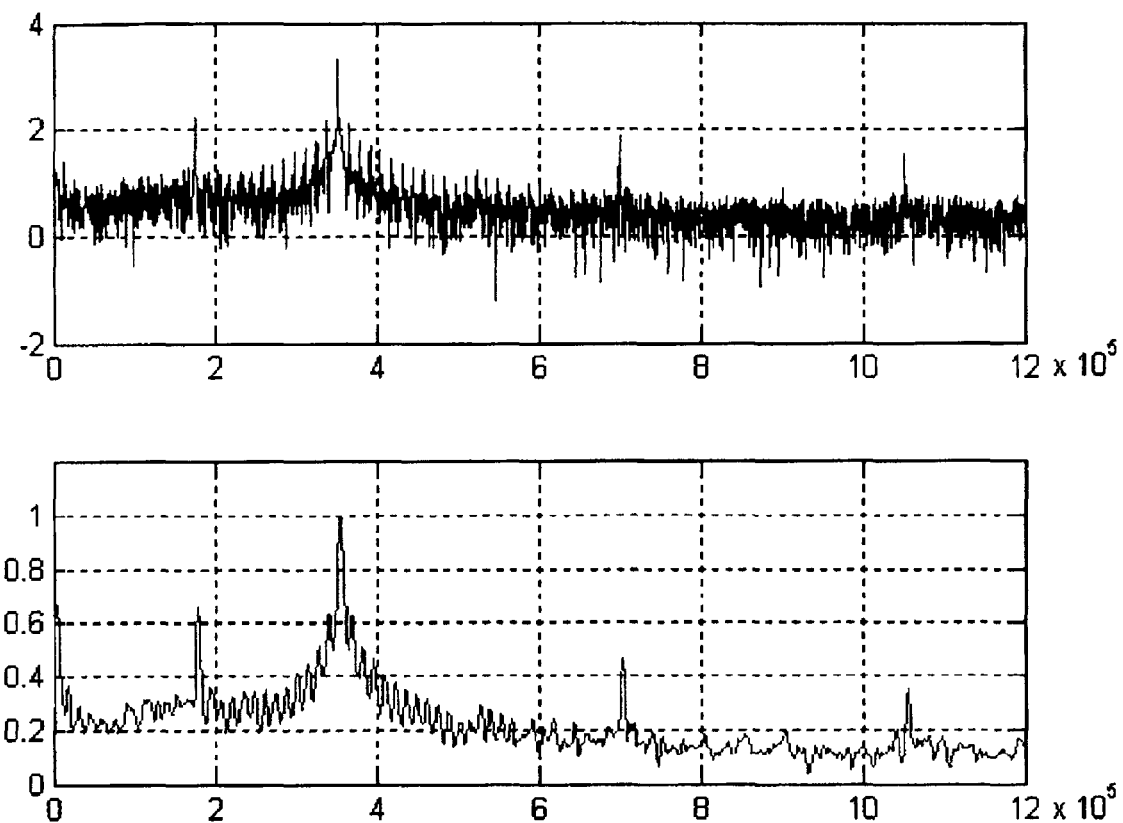

FIGS. 8A and 8B show the results for the first step of the method. In this step, the three transducers were operated at frequencies of 350 kHz, 700 kHz, and 1050 kHz respectively (at different power levels). The signals were applied in a cyclic manner for 3.2 msec ON, 36 msec OFF, 3.2 msec ON, etc. FIG. 8A shows the power spectrum recorded after 1 sec and FIG. 8B after 2 sec. The presence of microbubbles in the sample is detected by the appearance of energy peaks corresponding to the half harmonics of the primary frequencies. The presence of the line at 175 kHz in FIG. 8B clearly establishes that a significant population of microbubbles has been created in the sample after 2 sec.

Figure 9A:
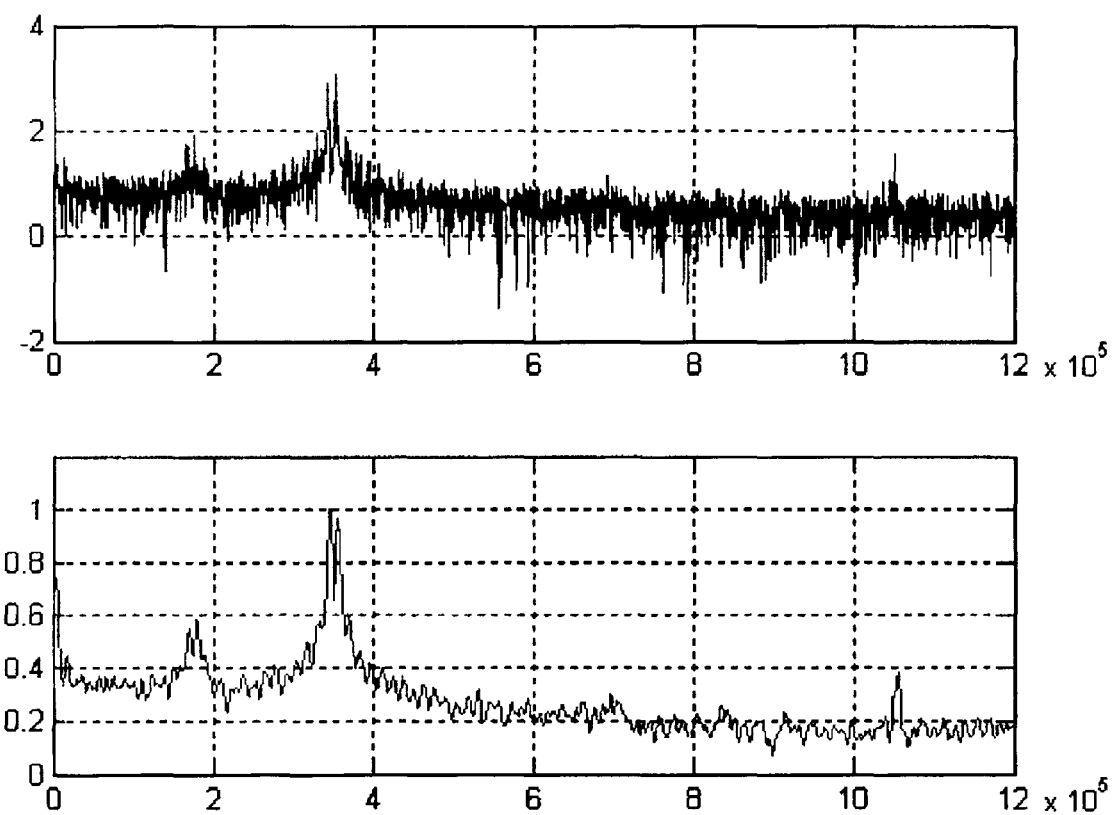
FIG. 9A and FIG. 9B are power spectrum of the echoes from microbubbles produced in fat in step two of the method of the invention.
Figure 9B:
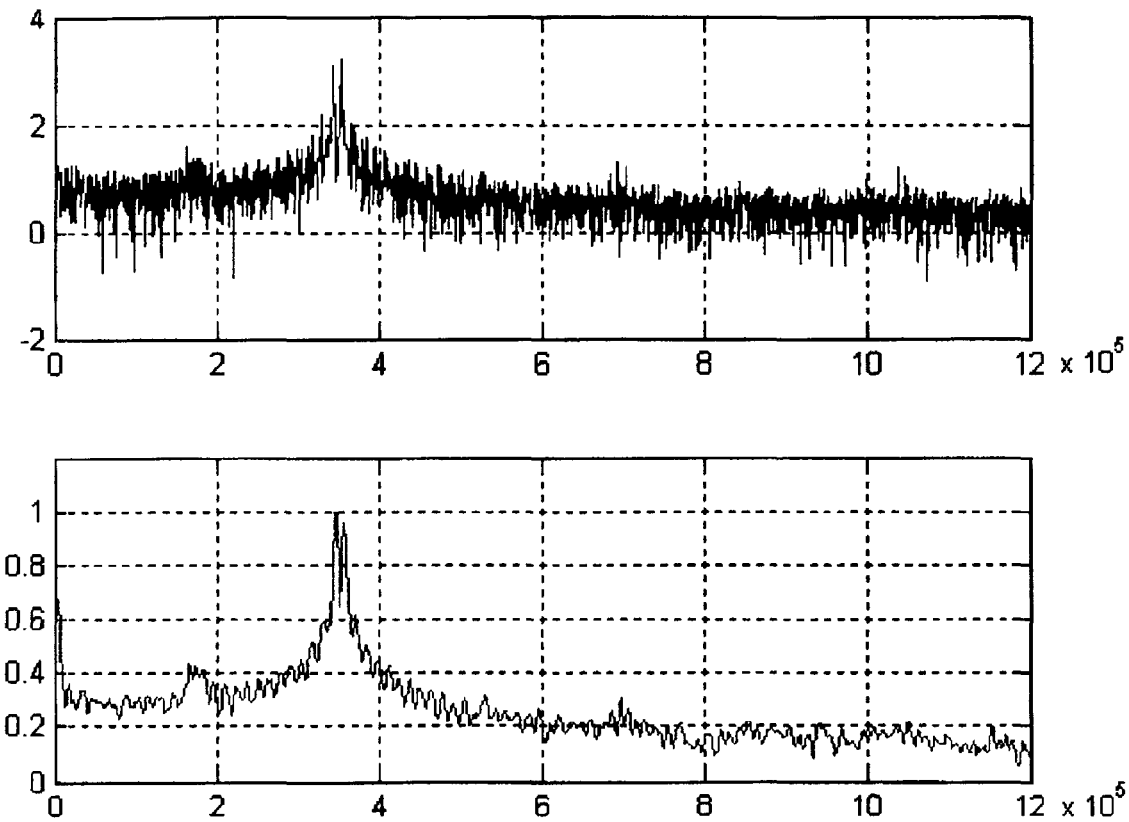

FIGS. 9A and 9B show the results for the second step of the method. In this step, one of the transducers was operated at frequencies of 350 kHz and 360 kHz and the other two transducers were "shut down". The signals were applied in a cyclic manner for 6.4 msec ON, 75 msec OFF, 6.4 msec ON, etc. FIG. 8A shows the power spectrum recorded after 2 sec and FIG. 8B after 5 sec. Observing the changes in the strength of line at 175 kHz, it can be seen that the waveform applied in this step caused enhancement of the cavitation and implosion of the microbubbles in the fat, until the population of microbubbles that were created in step 1, virtually disappeared after 5 sec of step 2.

Although embodiments of the invention have been described by way of illustration, it will be understood that the invention may be carried out with many variations, modifications, and adaptations, without departing from its spirit or exceeding the scope of the claims.

The invention claimed is:

1. A method of enhancing the cavitational effect produced by ultrasound signals focused at a specific location in a medium, said method comprising the following steps:

(a) using one or more transducers to apply said ultrasound signals to create a waveform that causes formation of bubbles at said location; and (b) modulating the amplitude of said ultrasound signals at a frequency between 5 KHz and 25 KHz immediately following or coincident with the formation of said bubbles such that the waveform causing the production of bubbles is a waveform comprising negative peaks and positive peaks, wherein the negative peaks are greater in absolute value than the positive peaks.

2. A method according to claim 1, wherein the modulation is carried out in one of the following two ways:

(a) combination of two or more interfering primary beams emitted from two or more transducers having a common focus; and (b) exciting individual transducers by an excitation pulse composed of two excitation pulses with closely proximate frequencies.

3. A method according to claim 1, wherein, if the number of transducers is more than one, then the different frequencies emitted by said transducers are integral multiples of the lowest of said frequencies.

4. A method according to claim 1, wherein the number of transducers is three.

5. A method according to claim 1, wherein the radius of the microbubbles is in the range from a fraction of a micron up to 100 or more microns.

6. A method according to claim 1, wherein the radius of the microbubbles is in the range from approximately 3 microns to 5 microns.

7. A method according to claim 1, wherein an ultrasound imaging or non-imaging system is used to view and monitor the region being targeted, to monitor the generation of the microbubbles at the desired location, and control the system for one or more of the following purposes:

(a) for aiming the focused beam to enable generating the microbubbles at the targeted location;

(b) to insure that the number of microbubbles is as planned;

(c) to re-align the beam to a different location; and (d) to monitor the formation, maintenance, or implosion of the microbubbles for the purpose of controlling either continuously or intermittently the application of the waveform and/or the modulation signals that causes these processes in order to achieve the planned result.

8. A method according to claim 7, wherein the response at the half harmonic or at higher harmonics of the transmitted frequencies is used by the ultrasound imaging or non-imaging system to measure one or both of the following:

(a) the number of microbubbles generated within the targeted region; and (b) the spatial distribution of said microbubbles generated within said targeted region.

9. A method according to claim 1, wherein the multiple transducers are arranged as an array, designed so that their mechanical focus and their own focus combine at the same point in space.

10. A method according to claim 9, wherein the array is an annular array.

11. A method according to claim 9, wherein the point in space can be moved axially or laterally by either shifting the whole array, by repositioning of individual transducers, or by phase shift of the excitation pulse.

12. A method according to claim 11, wherein the region within the focal zone of all the transducers in which the specific waveform develops at significant intensities and the amplitudes of the waveforms are less than −3 DB of the maximum amplitude, are typically at distances less than 25 mm and preferably less than 1 mm away from the point of said maximum amplitude in the lateral directions and less than 10 mm and preferably less than 1.5 mm away in the axial directions.

13. A method according to claim 9, wherein the ultrasonic waves transmitted by the different transducers are designed to produce in the microbubbles at the focal point interference that generates specific waveforms at specific frequencies and amplitudes, which are not produced at other locations.

14. A method according to claim 1, wherein the localized production of bubbles at the location and enhancement of the cavitational and implosion effects that take place at said location are for therapeutic purposes.

15. A method according to claim 1, wherein the one or more transducers are placed extra-corporally, in close proximity to the organ to be treated, with a spacer made of ultrasound-transparent material, ultrasound gel, or water surrounding said ultrasound transducer/s and filling the space between it and the surface of the body overlying said organ.

* * * * *